United States Patent [19]

Lê et al.

[11] Patent Number: 5,019,670

[45] Date of Patent: May 28, 1991

[54] PROCESS FOR PRODUCING ALKYLAROMATIC LUBRICANT FLUIDS

[75] Inventors: Quang N. Lê, Cherry Hill; Bruce P. Pelrine, Trenton; Joosup Shim, Wenonah, all of N.J.

[73] Assignee: Mobil Oil Corporation, Fairfax, Va.

[21] Appl. No.: 515,030

[22] Filed: Apr. 26, 1990

Related U.S. Application Data

[63] Continuation-in-part of Ser. No. 469,999, Jan. 25, 1990, Pat. No. 4,962,256, which is a continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ ............................ C07C 2/66; C07C 2/12
[52] U.S. Cl. ...................................... 585/467; 581/533
[58] Field of Search ........................... 585/467, 533, 10

[56] References Cited

U.S. PATENT DOCUMENTS

| | | | |
|---|---|---|---|
| 2,904,607 | 9/1959 | Mattox et al. | 260/671 |
| 3,251,897 | 5/1966 | Wise | 260/671 |
| 3,631,120 | 12/1971 | Eberly, Jr. et al. | 260/671 |
| 3,641,177 | 2/1972 | Eberly, Jr. et al. | 260/671 |
| 3,751,504 | 8/1973 | Keown et al. | 260/672 |
| 3,751,506 | 8/1973 | Burress | 260/671 |
| 3,755,483 | 8/1973 | Burress | 260/671 |
| 4,301,316 | 11/1981 | Young | 585/455 |
| 4,301,317 | 11/1981 | Young | 585/455 |
| 4,393,262 | 7/1983 | Kaeding | 585/467 |
| 4,439,409 | 3/1984 | Puppe et al. | 423/328 |
| 4,469,908 | 9/1984 | Burress | 585/467 |
| 4,826,667 | 5/1989 | Zones et al. | 423/277 |
| 4,899,008 | 2/1990 | LaPierre et al. | 585/467 |
| 4,912,277 | 3/1990 | Aufdembrink et al. | 585/467 |
| 4,935,574 | 6/1990 | D'Amore et al. | 585/467 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

*Primary Examiner*—Anthony McFarlane
*Attorney, Agent, or Firm*—Alexander J. McKillop; Charles J. Speciale; Malcolm D. Keen

[57] ABSTRACT

The thermal and oxidative stability of HVI-PAO olefin oligomers is improved by alkylation in the presence of a solid, porous, acidic alkylation catalyst defined by a specific X-ray diffraction pattern. A preferred catalyst is the synthetic zeolite MCM-22. The olefinic oligomers used as alkylating agents are prepared from 1-alkene oligomerization in contact with a reduced metal oxide, preferably reduced chromium oxide, catalyst on support such as silica. Aromatics which may be used in the reaction include monocyclic aromatics such as benzene and toluene as well as bicyclic aromatics such as naphthalene. Substituted aromatics may be used in order to introduce functional groups such as hydroxyl groups into the products, for example by the use of hydroxyaromtics such as phenol or naphthaol. The alkylated aromatic hydrocarbon products retain the unique features of the alkylating olefinic oligomer and exhibit high viscosity index and low pour point as well as improved thermal and oxidative stability and additive solvency characteristics.

24 Claims, 2 Drawing Sheets

PROCESS FOR PRODUCING ALKYLAROMATIC LUBRICANT FLUIDS

This application is a continuation-in-part of application Ser. No. 07/469,999, filed Jan. 25, 1990, of Q. N. Le et al. (now U.S. Pat. No. 4,962,256), which was a continuation-in-part of Ser. No. 07/254,524, filed Oct. 6, 1988, now U.S. Pat. No. 4,954,325. Ser. No. 07/254,524 was a continuation-in-part of Ser. No. 06/98,176, filed Sept. 18, 1987 (now abandoned), which was a continuation-in-part of Ser. No. 06/890,268, filed July 29, 1986 (now abandoned).

This application is also related to application Ser. No. 07/293,911, filed Jan.6, 1989, of S. C. Ho et al.

FIELD OF THE INVENTION

This invention relates to a process for producing alkylated aromatic compositions useful as lubricant basestock and lubricant additives. The invention also relates a process for producing lubricant compositions of high viscosity index (VI) and increased thermal stability by alkylating aromatics with high VI, low pour point poly-alpha-olefin oligomers.

BACKGROUND OF THE INVENTION

Efforts to improve upon the performance of natural mineral oil based lubricants by the synthesis of oligomeric hydrocarbon fluids have been the subject of important research and development in the petroleum industry for a large number of years and have led to the introduction of a number of superior polyalpha-olefin (PAO) synthetic lubricants produced by the oligomerization of alpha-olefins or 1-alkenes. In terms of lubricant property improvement, the thrust of the industrial research effort on synthetic lubricants has been toward fluids exhibiting useful viscosities over a wider range of temperature, i.e., improved viscosity index (VI), while also showing lubricity, thermal and oxidative stability and pour point equal to or better than mineral oil. These new synthetic lubricants exhibit lower friction characteristics and are therefore capable of increasing mechanical efficiency of various types of equipment including engines, transmissions, worm gears and traction drives, doing so over a wider range of operating conditions than mineral oil lubricants.

Notwithstanding their generally superior properties, PAO lubricants are often formulated with additives to enhance those properties for specific applications. Among the more commonly used additives are oxidation inhibitors, rust inhibitors, metal passivators, antiwear agents, extreme pressure additives, pour point depressants, detergent dispersants, viscosity index (VI) improvers, foam inhibitors and the like. This aspect of lubricant technology is described in Kirk-Othmer "Encyclopedia of Chemical Technology", 3rd Edition, Vol. 14, pp. 477-526, to which reference is made for a description of the use of such additives.

Improvements in synthetic lubricant technology have resulted both from new additive developments intended to address deficiencies in the lubricant (oligomer) basestocks as well as from developments in new base fluid (oligomer). Recently, lubricant compositions (referred to in this specification as HVI-PAO) of remarkable high VI coupled with low pour point have been developed. These lubricant compositions are described in U.S. Pat. Nos. 4,827,064 and 4,827,063, to which reference is made for a detailed description of these lubricants, methods for their preparation and of their properties and uses. These HVI-PAO materials comprise polyalpha-olefin oligomers prepared by the use of a reduced metal oxide, preferably reduced chromium, oligomerization catalyst. The lubricant product is characterized by a branch ratio less than 0.19, indicating a high degree of linearity and pour point below $-15°$ C. In its as-synthesized form, the HVI-PAO oligomer has olefinic unsaturation associated with the last of the recurring monomer units in the structure and this can be removed by a simple hydrogenative treatment to produce a stabilized, fully saturated oligomer product. Lubricants produced by the process cover the full range of lubricant viscosities and exhibit a remarkably high VI and low pour point even at high viscosity. Products of higher viscosity can also be produced by operating the oligomerization process at lower temperatures, typically $-20°$ to $+90°$ C., and these high viscosity products are useful as lubricant additives, especially VI improvers for both mineral and synthetic oils, as described in copending application Ser. No. 07/345,606, filed May 1, 1989, to which reference is made for a description of these higher viscosity oligomers, their properties and uses and of the method by which they may be made.

The process for preparing the HVI-PAO lubricants comprises, as noted above, contacting a $C_6$-$C_{20}$ 1-alkene feedstock with reduced valence state chromium oxide catalyst on porous silica support under oligomerizing conditions in an oligomerization zone to produce the high viscosity, high VI liquid hydrocarbon lubricant with branch ratios less than 0.19 and pour points below $-15°$ C. The oligomerization temperature is typically maintained at a value between 90° and 250° C. to produce the lubricant viscosity products. By operating the oligomerization process at lower temperatures, however, higher viscosity materials may be produced and these materials may be used as viscosity index (VI) improvers for lubricants, both of mineral oil and synthetic origin, as described application Ser. No. 07/345,606, filed May 1, 1989. The higher viscosity HVI-PAO products described in application Ser. No. 07/345,606 typically have viscosities between 725 and 15,000 cS at 100° C., corresponding to weight molecular weights from about 15,000 to 200,000 and number molecular weights from about 5,000 to about 50,000; carbon numbers for these molecular weights are from about $C_{30}$ to about $C_{10,000}$, with a preferred range from about $C_{30}$ to about $C_{5,000}$. Like the liquid lubricant oligomers, these higher molecular weight oligomers are characterized by high VI coupled with excellent low temperature fluidity properties including pour point for the liquid products.

Although these HVI-PAO oligomers have excellent fluid flow properties, as evidenced by their high VI values and low pour points, they do not necessarily possess the highest degree of thermal and oxidative stability under the most stringent conditions. For this reason, it would be desirable to improve their stability in these respects if this could be done without significant deterioration of their excellent rheological characteristics.

Alkylated aromatics, particularly alkylated naphthalene are known to possess good thermal and oxidative stability as disclosed in U.S. Pat. Nos. 4,211,665, 4,238,343, 4,604,491 and 4,714,7944 but these naphthalene derivatives do not usually possess good rheological properties: in particular, they have extremely poor VI, consonant with their aromatic character. The antiwear properties of alkylnaphthalene lubricating fluids are described in Khimiya i Tekhnologiya Topliv i Masel, No. 8, pp. 28-29, August, 1986 and are reported to show some promise as base stocks for lubricants. In general, however, alkylated naphthalenes have been disappointing as lubricants although their good thermal and oxidative stability have made them suitable for use as transformer oils and heat exchange media.

In co-pending application Ser. No. 07/293,911, filed January 6, 1989, there is described a method of improving the thermal and oxidative stability of the HVI-PAO oligomers by alklating the unsaturated oligomer product with an aromatic compound such as benzene or naphthalene. The products have the enhanced stability and good solvency characteristics associated with the aromatic component while retaining the excellent rheological characteristics of the HVI-PAO oligomers. According to the method described in application Ser. No. 07/293,911, the HVI-PAO oligomer is reacted with the aromatic compound in the presence of an alkylation catalyst such as a Lewis acid e.g. aluminum trichloride or born trifluoride or a solid acidic zeolite such as zeolite Y.

SUMMARY OF THE INVENTION

We have now found that the thermal and oxidative stability of the HVI-PAO oligomers may be improved by alkylation of aromatic compounds with the unsaturated oligomer using, as the alkylation catalyst, a solid, acidic catalyst which comprises a synthetic porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms. A preferred catalyst of this type includes the synthetic zeolite identified in this specification as MCM-22.

The alkylated products have been found to possess good thermal and oxidative stability as well as good additive solvency characteristics in addition to their characteristically excellent fluid flow properties: the HVI-PAO alkylated aromatic hydrocarbons retain the unique structurally-related features of the HVI-PAO olefinic oligomer and thereby exhibit an extraordinary combination of properties relating to high viscosity index and low pour point which makes them very useful as lubricant base stock.

The alkylated products can be prepared using very low to very high viscosity HVI-PAO as the alkylating agents for monocyclic or bicyclic aromatics such as benzene or naphthalene. Depending upon the HVI-PAO molecular weight range and the substituent groups on the aromatic nucleus, useful lubricant additives can be prepared for improved antiwear properties, antioxidant and other properties. The HVI-PAO alkyl-aromatic hydrocarbon has a significantly reduced degree of unsaturation. Accordingly, hydrogenation of the product to provide stable lube base stock can be eliminated for high viscosity materials but may be carried out if desired and is, in any event desirable for the lower viscosity materials.

The alkylated aromatic hydrocarbons have the structure:

where at least one R group is the hydrocarbyl residue of the polymerization of $C_2$-$C_{20}$ 1-alkene. This residue typically has a branch ratio less than 0.19, a weight average molecular weight between 280 and 450,000, number average molecular weight between 280 and 180,000, molecular weight distribution between 1 and 5. The remaining R groups are hydrogen, $C_1$-$C_{20}$ cyclic or acyclic alkyl and alkenyl, aryl, $NH_2$, acylamido, halogen, acyl, $NO_2$, YO where Y is hydrogen, acyl, alkoxycarbonyl, phenyl and $C_1$-$C_{20}$ cyclic or acyclic alkyl and alkenyl.

DETAILED DESCRIPTION

Olefin Oligomer

In the present process for producing the HVI-PAO products of improved thermal and oxidative stability aromatic hydrocarbons are alkylated with the unique olefin oligomers produced from the oligomerization of 1-alkenes over a reduced metal oxide catalyst, usually reduced chromium oxide on a silica support. As oligomerized, these HVI-PAO oligomers are mixtures of dialkyl vinylidenic and 1,2 dialkyl or trialkyl mono-olefin oligomers. Oligomerization of the olefin feed with the reduced metal oxide catalysts leads to an oligomer which is substantially free of double bond isomerization and has a high degree of linearity. Conventional PAO, on the other hand, formed by oligomerization over Lewis acid catalysts such as $BF_3$ or $ALCl_3$, are formed by a carbonium ion which, in turn, promotes isomerization of the olefinic bond and the formation of multiple isomers of lower linearity, as shown by their branch ratios of above 0.19, as compared to a ratio of 0.20 or higher for conventional PAO oligomers produced with Lewis acid catalysts.

Olefins suitable for use as starting material in the preparation of olefinic HVI-PAO oligomers useful as starting material in the present invention include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-hexene to 1-hexadecene and more preferably 1-octene to 1-tetradecene, or mixtures of such olefins.

In the oligomerization process, the olefin feed is contacted with the oligomerization catalyst to produce the desired oligomer product. In the preparation of the liquid hydrocarbons suitable as lubricant basestocks an alpha-olefin feedstock comprising olefins of 6 to 20 carbon atoms, or mixtures of such olefins, is contacted with the oligomerization catalyst under oligomerization conditions, at a reaction temperature between 90° to 250° C. dependent upon the desired product viscosity. The higher viscosity products are made at oligomerization temperatures from about $-20°$ to about $+90°$ C., with the exact temperature selected being dependent upon the viscosity desired in the product. Thus, in general, the oligomerization temperature may be from about $-20°$ to about 250° C., depending upon the characteristics, especially the viscosity, desired for the product.

In each case, the catalyst comprises a reduced metal oxide on a porous, solid support. The oxide is derived from a metal of Group VIB, preferably chromium, as the catalytic component on a porous support. The catalyst may be activated by treatment including oxidation at a temperature of 200° C. to 900° C. in the presence of an oxidizing gas and then by treatment with a reducing agent at a temperature and for a time sufficient to reduce the metal to a lower valence state. The catalyst most preferred is a lower valence Group VIB metal oxide on a porous inert support. Preferred supports include silica, alumina, titania, silica alumina, magnesia and the like. The support material binds the metal oxide catalyst. Those porous substrates having a pore opening of at least 40 Å are preferred.

The support material usually has high surface area and large pore volumes with average pore size of 40 to about 350 Å. The high surface area are beneficial for supporting large amount of highly dispersive, active chromium metal centers and to give maximum efficiency of metal usage, resulting in very high activity catalyst. The support should have large average pore openings of at least 40 Å, with an average pore opening of 60 to 300 Å preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B, R_2Mg$, RLi, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged with air at successively higher temperatures to about 600° for a period of about 16 to 20 hours. Thereafter the catalyst is cooled down under an inert atmosphere to a temperature of about 250° to 450° C. and a stream of reducing agent such as CO or $H_2$ is contacted therewith for a period to reduce the catalyst as indicated by a distinct color change from bright orange to bluish green. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices in the lubricant products. These low branch ratios are also correlated with the lour points of the lubricant products.

The branch ratios are defined as the ratios of $CH_3$ groups to $CH_2$ groups in the oligomers are calculated from the weight fractions of methyl groups obtained by infrared methods, published in *Analytical Chemistry.* Vol. 25, No. 10, p. 1466 (1953).

$$\text{Branch ratio} = \frac{\text{wt. fraction of methyl group}}{1 - (\text{wt fraction of methyl group})}$$

In general, the HVI-PAO oligomers have the following regular head-to-tail structure where n is preferably 0 to 17, terminating in olefinic unsaturation:

with some head-to-head connections. The as-synthesized HVI-PAO molecular structure generally has one double bond unsaturation. The HVI-PAO process also produces a surprisingly simpler and useful dimer compared to the dimer produced by 1-alkene oligomerization with BF₃ or AlCl₃ as commercially practiced. Typically, in the present invention it has been found that a significant proportion of unhydrogenated dimerized 1-alkene has a vinylidenyl structure as follows.

$$CH_2=CR_1R_2$$

where $R_1$ and $R_2$ are alkyl groups representing the residue from the head-to-tail addition of 1-alkene molecules. For example, 1-decene HVI-PAO dimer, which can be used as alkylating olefin in the present invention, has been found to contain only three major components, as determined by GC. Based on $C^{13}$ NMR analysis, the unhydrogenated components were found to be 8-eicosene, 9-eicosene, 2-octyldodecene and 9-methyl-8 or 9-methyl-9-nonadecene.

The liquid lubricant compositions produced by the oligomerization process at relatively high oligomerization temperatures e.g. between 90° and 250° C., comprise $C_{30}$–$C_{1300}$ hydrocarbons, with branch ratios of less than 0.19, weight average molecular weights between 300 and 45,000, number average molecular weights between 300 and 18,000. The molecular weight distribution of these oligomers is between 1 and 5 and the pour point of the liquid lubricants is below −15° C.

The HVI-PAO oligomers, in the broadest terms, have a weight average molecular weight between 280 and 450,000 and number average molecular weight between 280 and 180,000. Measured in carbon numbers, molecular weights range from $C_{20}$ to $C_{10000}$ and viscosity up to 7500 cs at 100° C., with a preferred range of $C_{30}$ to $C_{1000}$ and a viscosity of up to 1000 cs at 100° C. for lube base stock material. Molecular weight distributions (MWD), defined as the ratio of weight average molecular to number average molecular weight, range from 1.00 to 5, with a preferred range of 1.01 to 3 and a more preferred MWD of about 1.05 to 2.5. The viscosities of the olefinic HVI-PAO oligomers used as alkylating agents in the present process will typically range from 1.5 cS to 7500 cS (measured at 100° C.).

Usually, the lubricant range oligomers are produced by varying the oligomerization temperature to yield lubricant viscosity range oligomers having weight average molecular weight between 420 and 45,000 and number average molecular weight between 420 and 18,000. Measured in carbon numbers, molecular weights range from $C_{30}$ to $C_{1300}$ and a viscosity up to 750 cs at 100° C., with a preferred range of $C_{30}$ to $C_{1000}$ and a viscosity of up to 500 cS at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5. Compared to conventional PAO derived from BF₃- or AlCl₃-catalyzed polymerization of 1-alkene, HVI-PAO has been found to have a higher proportion of higher molecular weight polymer molecules in the product.

The viscosities of the lubricant HVI-PAO oligomers measured at 100° C. range from 3 cS to 5000 cS. The viscosity index for the liquid polyalpha-olefins is approximately described by the following equation:

$$VI = 156.8 + 4.94 \times (V_{100° C.})^{0.5},$$

where $V_{100°}$ C. is the kinematic viscosity in centistokes measured at 100° C.

The higher viscosity oligomers produced at oligomerization temperatures below about 90° C. comprise hydrocarbons which have a branch ratio below 0.19 and a viscosity at 100° C. which is typically from 100 to 20,000 cS. The hydrocarbons typically have weight average molecular weights from 15,000 to 200,000 and number average molecular weights from 5,000 to 50,000 with a molecular weight distribution from about 1 to about 5. The viscosity index of the liquid compositions of this type is at least 130 and usually higher, for example, above 180 or even 200 or higher. The high viscosity materials are characterized by high shear stability, being stable under high temperature, high shear rate conditions, notably at 150° C. and a shear rate of one million ($10^6$) reciprocal seconds. Reference is made to Ser. No. 07/345,606 for a more detailed description of these oligomers, their properties and uses as well of the methods by which they may be made.

When the HVI-PAO oligomers are to be used directly as lubricants or lubricant additives, they are usually hydrogenated after the oligomerization to improve stability by removal of residual unsaturation. As oligomerized, the HVI-PAO oligomers are mixtures of dialkyl vinylidenic and 1,2 dialkyl or trialkyl mono-olefins and the lower molecular weight unsaturated oligomers are preferably hydrogenated to produce the thermally and oxidatively stable lubricants. The higher molecular weight unsaturated HVI-PAO oligomers are usually sufficiently thermally stable to be utilized without hydrogenation and, optionally, may be so employed. Both unsaturated and hydrogenated HVI-PAO of lower or higher molecular exhibit viscosity indices of at least 130 and pour point below −15° C.

The oligomer may be stripped after the oligomerization process is complete in order to remove unreacted olefin and any low molecular weight dimer material.

Examples 1 to 8 below illustrate the production of the HVI-PAO olefin oligomers.

Aromatic Component

In the present process, the thermal and oxidative stabilities and solvency characteristics of the oligomers are improved by using the oligomer in its unhydrogenated condition to alkylate an aromatic substrate, usually a monocyclic or bicyclic aromatic compound in the presence of a solid, acidic alkylation catalyst. Aromatic compounds which may be used include substituted and unsubstituted benzene compounds such as benzene itself, toluene, the isomeric xylenes, ethylbenzene, cumene and bicyclic polycyclic aromatic compounds, particularly naphthalene, anthracene and phenanthracene. Typical useful aromatic hydrocarbons for the present invention include benzene, toluene, o,m,p-xylene, hemimellitene, pseudocumene, ethylbenzene, n-propylbenzene, cumene, n-butylbenzene, isobutylbenzene, sec-butylbenzene, tert-butylbenzene, p-cymene, biphenyl, diphenylmethane, triphenyl methane, 1,2-diphenylethane and similarly alkyl substituted naphthalenes and anthracenes; also phenol, catechol, acylphenol such as acetylphenol, carbonate esters such as phenyl methyl or ethyl carbonate and diphenyl carbonate, alkylphenol such as anisole, chloro and bromobenzene, aniline, acyl aniline such as acetanilide, methyl and ethylbenzoate, thiophenol and acylated thiophenol, nitrobenzene, diphenylether, diphenylsulfide and similarly substituted naphthalenes and anthracenes, in particular naphthols such as mono and dihydroxy naphthalene.

Alkylation Catalyst

The alkylation process is carried out in the presence of a solid, porous acidic catalytic material which a characteristic X-ray diffraction pattern. In its calcined form, the synthetic porous crystalline material component employed in the catalyst is characterized by an X-ray diffraction pattern including the lines shown in Table 1 below:

TABLE 1

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines shown in Table 2 below:

TABLE 2

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines shown in Table 3 below:

TABLE 3

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines shown in Table 4 below:

TABLE 4

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensites, 100 $I/I_o$, where $I_o$ is the intensity of the strongest line or peak, and d (obs.) the interplanar spacing in Angstrom Units (Å), corresponding to the recorded lines, were determined. In Tables 1-4, the relative intensities are given in terms of the symbols W=weak, M=medium, S=strong, VS=very strong. In terms of intensities, these may be generally designated as follows:

W=0-20
M=20-40
S=40-60
VS=60-100

These X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, to which reference is made for a description of this material as well as of its preparation. Another crystalline material of this type is the synthetic zeolite MCM-22.

Zeolite MCM-22 has a chemical composition expressed by the molar relationship:

$$X_2O_3:(n)YO_2,$$

where X is a trivalent element, such as aluminum, boron, iron and/or gallium, preferably aluminum, Y is a tetravalent element such as silicon and/or germanium, preferably silicon, and n is at least about 10, usually from about 0 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

where R is an organic component. The Na and R components are associated with the zeolite as a result of their presence during crystallization, and are easily removed by the post-crystallization methods described below.

Zeolite MCM-22 is thermally stable and exhibits a high surface area greater than about 400 $m^2/gm$ as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced at least in part by established techniques including ion exchange with other cations. Preferred replacement cations include metal ions, hydrogen ions, hydrogen precursor ions, e.g., ammonium and mixtures of such ions.

In its calcined form, zeolite MCM-22 appears to be made up of a single crystal phase with little or no detectable impurity crystal phases and has an X-ray diffraction pattern including the lines listed in above Tables 1-4.

Prior to its use as alkylation catalyst, the zeolite crystals should be subjected to thermal treatment to remove part or all of any organic constituent present in the as-synthesised material.

The zeolite in its as-synthesised form containing organic cations as well as when it is in its ammonium form, can be converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to a limit imposed by the irreversible thermal degradation of the crystalline structure of the zeolite, typically up to about 925° C.

Prior to its use in the alkylation process, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, described below, and water. The reaction mixture has a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

The organic directing agent for use in synthesizing zeolite MCM-22 from the above reaction mixture is hexamethyleneimine.

In a preferred method of synthesizing zeolite MCM-22, the $YO_2$ reactant contains a substantial amount of solid $YO_2$, e.g., at least about 30 wt.% solid $YO_2$. Where $YO_2$ is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt%; free $H_2O$ and about 4.5 wt.% bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days, after which the crystals are separated from the liquid and recovered.

The reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the alkylation process of this invention. Such materials include active and inactive materials and synthetic or naturally occurring zeolites as well as inorganic materials such as clays and/or oxides such as alumina, silic or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that alkylation products can be obtained economically and orderly without employing other means for controlling the rate of reaction. These materials may be incorporated into naturally occurring clays, e.g., bentonite and kaolin, to improve the crush strength of the catalyst under commercial alkylation operating conditions and function as binders or matrices for the catalyst. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst used in the present process may be increased by steaming. U.S. Pat. Nos. 4,663,492; 4,594,146; 4,522,929; and 4,429,176, describe conditions for the steam stabilization of zeolite catalysts which can be utilized to steam-stabilize the catalyst. Reference is made to these patents for a detailed description of the steam stabilization technique for use with the present catalysys. The steam stabilization conditions typically include contacting the catalyst with, e.g., 5-100% steam at a temperature of at least about 300° C. (e.g., 300°-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. The steaming of the catalyst can take place under conditions sufficient to initially increase the Alpha Value of the catalyst, the significance of which is discussed below, and produce a steamed catalyst having an enhanced Alpha Value. If desired, steaming can be continued to subsequently reduce the Alpha Value from the higher Alpha Value to an Alpha Value which is substantially the same as the Alpha Value of the unsteamed catalyst.

The preparation of various MCM-22 catalytic materials is described in detail in Examples 9 to 16 below. In these Examples illustrating the synthesis of zeolite, sorption data for water, cyclohexane and/or n-hexane adsorption were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt.% for water vapor, greater than about 4.5 wt.%, usually greater than about 7 wt.% for cyclohexane vapor and greater than about 10 wt.% for n-hexane vapor. These vapor sorption capacities are a notable distinguishing feature of zeolite MCM-22 and are preferred for the zeolite component of catalyst for use herein.

The Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec $^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), to which reference is made for that description. The experimental conditions of the test reported here include a constant temperature of 538° C. and a variable flow rate as described in detail in the *Journal of Catalysis*, Vol. 61, p. 395.

Alkylation

The alkylation of the aromatic compound with the HVI-PAO oligomer is suitably effected by contact of the reactants at a temperature of between about 0° C. and about 500° C., and preferably between about 50° C. and about 250° C. The reaction generally takes place at pressures of from about 0.2 to about 250 atmospheres and preferably from about 1 to about 25 atmospheres. The molar ratio of alkylatable aromatic compound to olefin oligomer alkylating agent can typically be from about 0.1:1 to about 50:1, and preferably can be from about 0.5:1 to about 5:1. Reaction is suitably accomplished utilizing a feed weight hourly space velocity (WHSV) of between about 0.1 hr$^{-1}$ and about 500 hr$^{-1}$ and preferably from 0.5 hr$^{-1}$ to about 100 hr$^{-1}$. The latter WHSV is based upon the total weight of active catalyst (and binder if present). The alkylation can be carried out as a batch-type, semi-continuous or continuous operation utilizing a fixed, fluidized or moving bed catalyst system.

The alkylation is carried out using the unhydrogenated oligomer and during the course of the alkylation reaction, the residual unsaturation in the oligomer is mostly eliminated, so that the alkylation product is almost completely saturated although some residual unsaturation may remain, indicative of incomplete reaction. This residual unsaturation may be removed by hydrotreating, if desired.

Alkylation Products

The alkylated aromatic compounds which are produced by the process typically have the structure:

-continued and where at least one R group is the hydrocarbyl HVI-PAO residue derived from the polymerization of $C_2$–$C_{20}$ 1-alkene. This residue will have a branch ratio less than 0.19, weight average molecular weight between 300 and 45,000, number average molecular weight between 300 and 18,000, a molecular weight distribution between 1 and 5. he remaining R groups are hydrogen, $C_1$–$C_{20}$ cyclic or acyclic alkyl and alkenyl, aryl, $NH_2$, acylamido, halogen, acyl, $NO_2$, YO and YS where Y is hydrogen, azyl, alkoxycarbonyl, phenyl or $C_1$–$C_{20}$ cyclic or acyclic alkyl and alkenyl.

Generally, the hydrocarbyl HVI-PAO residue in the formula above comprises a vinylidenyl radical having the structure:

$R_1R_2CH-CH_2-$ where $R_1$ and $R_2$ may be alike or different and comprises the HVI-PAO oligomeric moiety having a generally head-to-tail repeating structure of $C_2$–$C_{20}$ 1-alkenes with a $CH_3/CH_2$ ratio less than 0.20, preferably between 0.14 and 0.19.

The introduction of the aromatic groups, especially phenolic groups into the alpha olefin oligomers results in a highly useful class of lubricant basestock with superior thermal and oxidative stabilities, better additive solvency, seal swell characteristic and, depending on the nature of the aromatic compound, other properties such as antiwear properties, while maintaining the high VI and low pour properties. It also enables the conventional hydrofinishing step usually required for the lubricant basestock to be eliminated in favorable cases. The alkylaromatic products of the process are useful as lubricant basestock and as additives for both mineral and synthetic lubricants. The higher molecular weight products are especially useful as multipurpose lubricant additives since they have excellent VI improvement properties which may be combined with other valuable additive characteristics. The introduction of the aromatic moiety into the HVI-PAO increases thermal stability, increases solubilizing power of the product and may add other properties useful in additives such as antiwear properties and VI enhancement. Therefore, as additives, their usefulness is compounded to incorporate in a single additive product the capability to improve a lube basestock thermal stability, VI, solvency and seal swelling power as well as improving antiwear characteristics. They possess the further advantage of great flexibility in the range o. viscosity in which they can be prepared so that their additive properties can be used in a viscosity compatible with the viscosity formulation of the lube basestock.

Examples 17 to 22 below illustrate the preparation and properties of the alkylated HVI-PAO products.

Examples 1-8, immediately following, illustrate the preparation of HVI-PAO oligomers.

EXAMPLE 1

Catalyst Preparation and Activation Procedure 1.9 grams of chromium (II) acetate $(Cr_2(OCOCH_3)_4 2H_2O)$ (5.58 mmole) (commercially obtained) is dissolved in 50 cc of hot acetic acid. Then 50 grams of a silica gel of 8–12 mesh size, a surface area of 300 $m^2/g$, and a pore volume of 1 cc/g, also is added. Most of the solution is absorbed by the silica gel. The final mixture is mixed for half an hour on a rotovap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$.

EXAMPLE 2

The powdered catalyst prepared in Example 1 (3.2 g) is packed in a ⅜" stainless steel tubular reactor inside an $N_2$ blanketed dry box. The reactor under $N_2$ atmosphere is then heated to 150° C. by a single-zone Lindberg furnace. Pre-purified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

The experiments conducted under the above condition of essentially constant temperature and WHSV produce HVI-PAO with about the same viscosity.

EXAMPLE 3

In a manner similar to that of Example 2, a fresh catalyst sample is charged into the reactor and 1-hexene is pumped to the reactor at 1 atm and 10 cc per hour. As shown below, a lube of high viscosities and high VI's is obtained. These runs show that at different reaction conditions, a lube product of high viscosities can he obtained and that viscosity can be varied with change in reaction temperature.

| Sample | A | B |
|---|---|---|
| T.O.S., hrs. | 20 | 44 |
| Temp., °C | 100 | 50 |
| Lube Yield, % | 8.2 | 8.0 |

-continued

| Sample | A | B |
| --- | --- | --- |
| Viscosities, cS at | | |
| 40° C. | 13170 | 19011 |
| 100° C. | 620 | 1048 |
| VI | 217 | 263 |

EXAMPLE 4

A commercial chromium/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
| --- | --- | --- | --- | --- |
| T.O.S., hrs. | 3.5 | 4.5 | 6.5 | 22.5 |
| Lube Yield, % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr/silica catalyst are also effective for oligomerizing olefins to lube products.

EXAMPLE 5

As in Example 4, purified 1-decene is pumped through the reactor at 250 to 320 psi. The product is collected periodically and stripped of light products boiling points below 650° F. High quality lubes with high VI are obtained (see following table). The table also shows that at about the same WHSV, the viscosity of the product decreases with increasing reaction temperature (135, 166, 197° C.)

| Reaction Temp. °C. | WHSV g/g/hr | Lube Product Properties | | |
| --- | --- | --- | --- | --- |
| | | V at 40° C. (cS) | V at 100° C. (cS) | VI |
| 120 | 2.5 | 1555.4 | 157.6 | 217 |
| 135 | 0.6 | 389.4 | 53.0 | 202 |
| 150 | 1.2 | 266.8 | 36.2 | 185 |
| 166 | 0.6 | 67.7 | 12.3 | 181 |
| 197 | 0.5 | 21.6 | 5.1 | 172 |

EXAMPLE 6

A commercial Cr on silica catalyst which contains 1% Cr on a large pore volume synthetic silica gel is used. The catalyst is first calcined with air at 700° C. for 16 hours and reduced with CO at 350° C. for one to two hours. 1.0 part by weight of the activated catalyst is added to 1-decene of 200 parts by weight in a suitable reactor and heated to 185° C. 1-Decene is continuously fed to the reactor at 2-3.5 parts/minute and 0.5 parts by weight of catalyst is added for every 100 parts of 1-decene feed.

After 1200 parts of 1-decene and 6 parts of catalyst are charged, the slurry is stirred for 8 hours. The catalyst is filtered and light product boiled below 150° C. @ 0.1 mm Hg is stripped. The residual product is hydrogenated with a Ni on Kieselguhr catalyst at 200° C. The finished product has a viscosity at 100° C. of 18.5 cs, VI of 165 and pour point of −55° C.

EXAMPLE 7

This was carried out as in Example 6, except that a reaction temperature is 125 ° C. The finished product has a viscosity at 100° C. of 145 cs, VI of 214, pour point of −40° C.

EXAMPLE 8

This was carried out as in Example 6, except that a reaction temperature is 100° C. The finished product has a viscosity at 100° C. of 298 cs, VI of 246 and pour point of −32° C.

The following Table summarizes the molecular weights and distributions of Examples 6 to 8.

| | Example No. | | |
| --- | --- | --- | --- |
| | 6 | 7 | 8 |
| V @ 100° C., cS | 18.5 | 145 | 298 |
| VI | 165 | 214 | 246 |
| Number-average molecular weights, $MW_n$ | 1670 | 2062 | 5990 |
| Weight-average molecular weights, $MW_n$ | 2420 | 4411 | 13290 |
| Molecular weight distribution, MWD | 1.45 | 2.14 | 2.22 |

Under similar conditions, HVI-PAO product with viscosity as low as 1.5 cs and as high as 7500 cs, with VI between 130 and 350, can be produced. Examples 9 to 16, immediate y following, illustrate the preparation of MCM-22 catalyst.

EXAMPLE 9

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO/Al_2O_3 = 30.0$
$OH^{-2}/SiO_2 = 0.18$
$H_2O/SiO_2 = 44.9$
$Na/SiO_2 = 0.18$
$R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table 5 below.

TABLE 5

| Degrees 2-Theta | Interplanar d-Spacing (A) | $I/I_o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |

TABLE 5-continued

| Degrees 2-Theta | Interplanar d-Spacing (A) | I/I$_o$ |
|---|---|---|
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

The sorption capacities of the calcined material were measured to be:

| | |
|---|---|
| H$_2$O | 15.2 wt. % |
| Cyclohexane | 14.6 wt. % |
| n-Hexane | 16.7 wt. % |

The surface area of the calcined crystalline material was measured to be 494 m$^2$/g.

The chemical composition of the uncalcined material was determined to be as follows:

| Component | Wt. % |
|---|---|
| SiO$_2$ | 66.9 |
| Al$_2$O$_3$ | 5.40 |
| Na | 0.03 |
| N | 2.27 |
| Ash | 76.3 |
| SiO$_2$/Al$_2$O$_3$, mole ratio | 21.1 |

A portion of the calcined crystalline product was tested in the Alpha Test and was found to have an Alpha Value of 224.

EXAMPLES 10–12

Three separate synthesis reaction mixtures were prepared with compositions indicated in Table 6 below. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table 6. The sorption and surface area measurements were of the calcined product.

TABLE 6

| | Example | | |
|---|---|---|---|
| | 10 | 11 | 12 |
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |

TABLE 6-continued

| | Example | | |
|---|---|---|---|
| | 10 | 11 | 12 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, molar | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

Quantities of the calcined (538° C. for 3 hours) crystalline silicate products of Examples 10, 11 and 12 were tested in the Alpha Test and found to have Alpha Values of 227, 180 and 187, respectively.

EXAMPLE 13

To demonstrate a further preparation of the zeolite MCM-22, 4.49 parts of hexamethyleneimine was added to a solution containing part 1 of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table 7. The surface area and sorption analyses were performed on the calcined sample, the chemical composition on the uncalcined material.

TABLE 7

| Product Composition | | |
|---|---|---|
| C | 12.1 | wt. % |
| N | 1.98 | wt. % |
| Na | 640 | ppm |
| Al$_2$O$_3$ | 5.0 | wt. % |
| SiO$_2$ | 74.9 | wt. % |
| SiO$_2$/Al$_2$O$_3$, mole ratio | 25.4 | |
| Adsorption, wt. % | | |
| Cyclohexane | 9.1 | |
| N-Hexane | 14.9 | |
| H$_2$O | 16.8 | |
| Surface Area, m$^2$/g | 479 | |

EXAMPLE 14

Twenty-five grams of solid crystal product of Example 14 were calcined in a flowing nitrogen atmospheres at 538° C. for 5 hours, followed by purging with 5% oxygen gas (balance N$_2$) for another 16 hours at 538° C.

Individual 3 g samples of the calcined material were ion-exchanged with 100 ml of 0.1 N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Ionic Composition, wt. % | Exchange Ions | | |
|---|---|---|---|
| | TEA | TPA | La |
| Na | 0.095 | 0.089 | 0.063 |
| N | 0.30 | 0.38 | 0.03 |
| C | 2.89 | 3.63 | — |
| La | — | — | 1.04 |

The La-exchanged sample was sized to 14 to 25 mesh and then calcined in air at 538° C. for 3 hours. The calcined material had an Alpha Value of 173.

The calcined sample of the La-exchanged material was severely steamed at 649° C. in 100% steam for 2 hours. The steamed sample had an Alpha Value of 22, demonstrating that the zeolite has very good stability under severe hydrothermal treatment.

EXAMPLE 15

This example illustrates the preparation of the zeolite MCM-22 where X in the general formula above is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:
$SiO/B_2O_3 = 6.1$
$OH^{-2}/SiO_2 = 0.06$
$H_2O/SiO_2 = 19.0$
$K/SiO_2 = 0.06$
$R/SiO_2 = 0.30$
where R is hexamethylenaimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| $H_2O$ (12 Torr) | 11.7 wt. % |
|---|---|
| Cyclohexane (40 Torr) | 7.5 wt. % |
| n-Hexane (40 Torr) | 11.4 wt. % |

The surface area of the calcined crystalline material was measured (BET) to be 405 $m^2/g$.

The chemical composition of the uncalcined material was determined to be as follows:

| N | 1.94 wt. % |
|---|---|
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al + B)_2O_3$, molar ratio | 25.8 |

A portion of the calcined crystalline product of was treated with $NH_4Cl$ and again calcined. The final crystalline product was tested in the Alpha Test and found to have an Alpha Value of 1.

EXAMPLE 16

This example illustrates another preparation of the zeolite in which X of the general formula above is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| $SiO_2/B_2O_3$ | 12.3 |
|---|---|
| $OH^-/SiO_2$ | 0.056 |
| $H_2O/SiO_2$ | 18.6 |
| $K/SiO_2$ | 0.056 |
| $R/SiO_2$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| $H_2O$ (12 Torr) | 14.4 wt. % |
|---|---|
| Cyclohexane (40 Torr) | 4.6 wt. % |
| n-Hexane (40 Torr) | 14.0 wt. % |

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

A portion of the calcined crystalline product was tested in the Alpha Test and found to have an Alpha Value of 5.

EXAMPLE 17

FIG. 3 is a schematic illustration of the alkylation process of this invention carried out with a high viscosity index 1-decene oligomer product obtained with $Cr/SiO_2$ catalyst (HVI-PAO).

The alkylation reaction was carried out with 500 g of the 1-decene oligomer in an alkylation reactor with benzene (95 g). The alkylation reactor contained 36 g zeolite MCM-22 and the reaction was carried out at 400 psig nitrogen and 400° F. for 6 hours, after which the catalyst was decanted and the unreacted benzene distilled off.

The properties of the decene oligomers before and after alkylation of the benzene are shown as follows:

| Lube Properties | HVI-PAO | Benzene/HVI-PAO |
|---|---|---|
| Pour Point, °F. | −30 | −25 |
| Cloud Point, °F. | <−65 | −30 |
| KV at 40° C., cSt | 122.9 | 68.11 |
| KV at 100° C., cSt | 18.33 | 11.60 |
| VI | 167 | 166 |

EXAMPLES 18-20

A 145 cS (100° C.) HVI-PAO olefin oligomer was used as the unhydrogenated starting material for a series of alkylation reactions using 1-methylnaphthalene as the aromatic substrate. All reactions were performed in glassware at atmospheric conditions. Reactants were combined and then heated to temperature with stirring. At the end of the reaction period, the catalyst, MCM-22, was filtered from the liquid. Distillation was done to remove any unreacted 1-methylnaphthalene and the alkylated product isolated.

Three different reaction temperatures were used as shown in Examples 18-20. In each case, the viscosity of the resulting product increased due to the incorporation of the aromatic function. At the same time, the viscosity index of the products remained virtually unchanged. Concurrent with the alkylation is the lowering of the bromine number. This is due to the addition of the aromatic to the double bond of the unhydrogenated HVI-PAO.

Thermal stability testing was conducted on the alkylated products. The test consisted of subjecting the samples to a temperature of 300° C. for a period of 24 hours in an inert atmosphere such as nitrogen. Following the thermal test the viscosities of the samples were determined and compared with the unalkylated 145 cS HVI-PAO feed. The viscosity loss results are shown in Table 8 below. The unalkylated feed lost 76% of its viscosity while the alkylated HVI-PAO show lower losses. Example 18 shows a substantially reduced viscosity loss of 31%.

Figure 1:
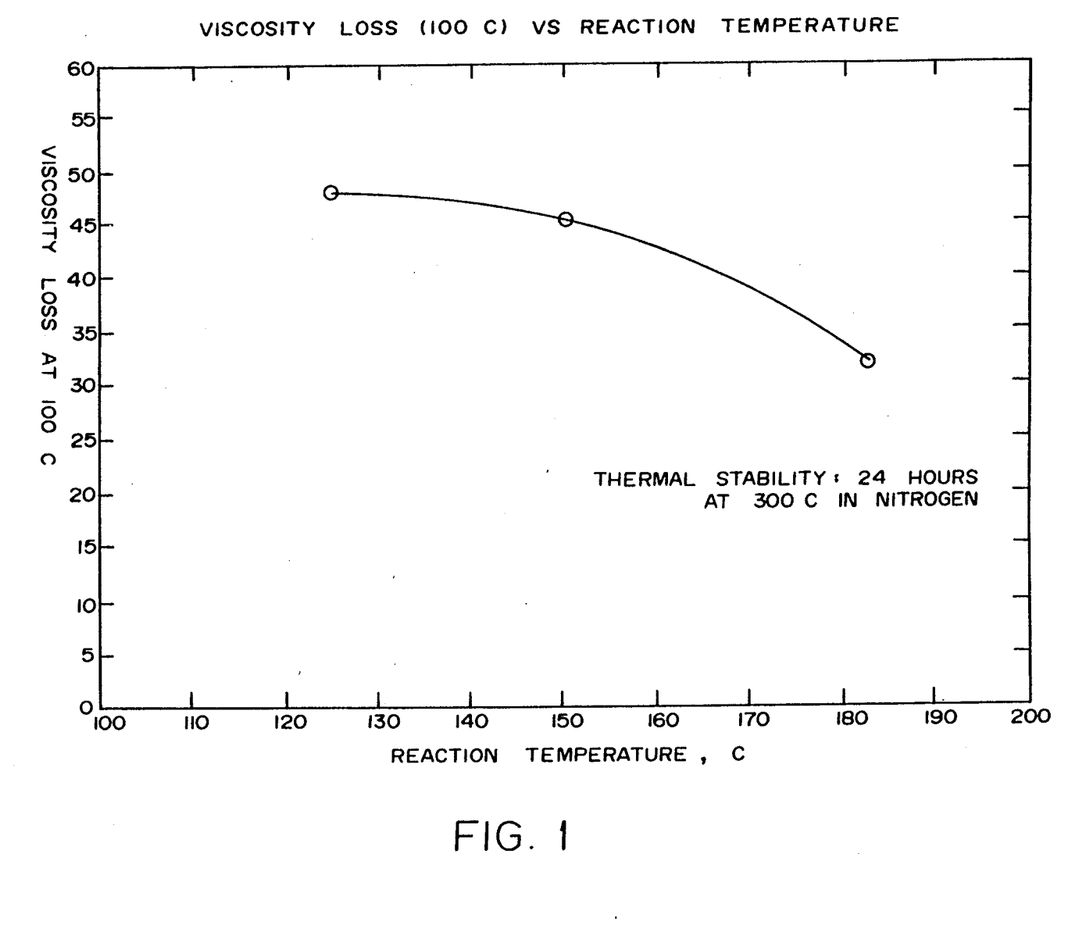
FIG. 1 is a graph showing the relationship between the reaction temperature in the alkylation and the corresponding effect on the thermal stability of the alkylated product.
Figure 2:
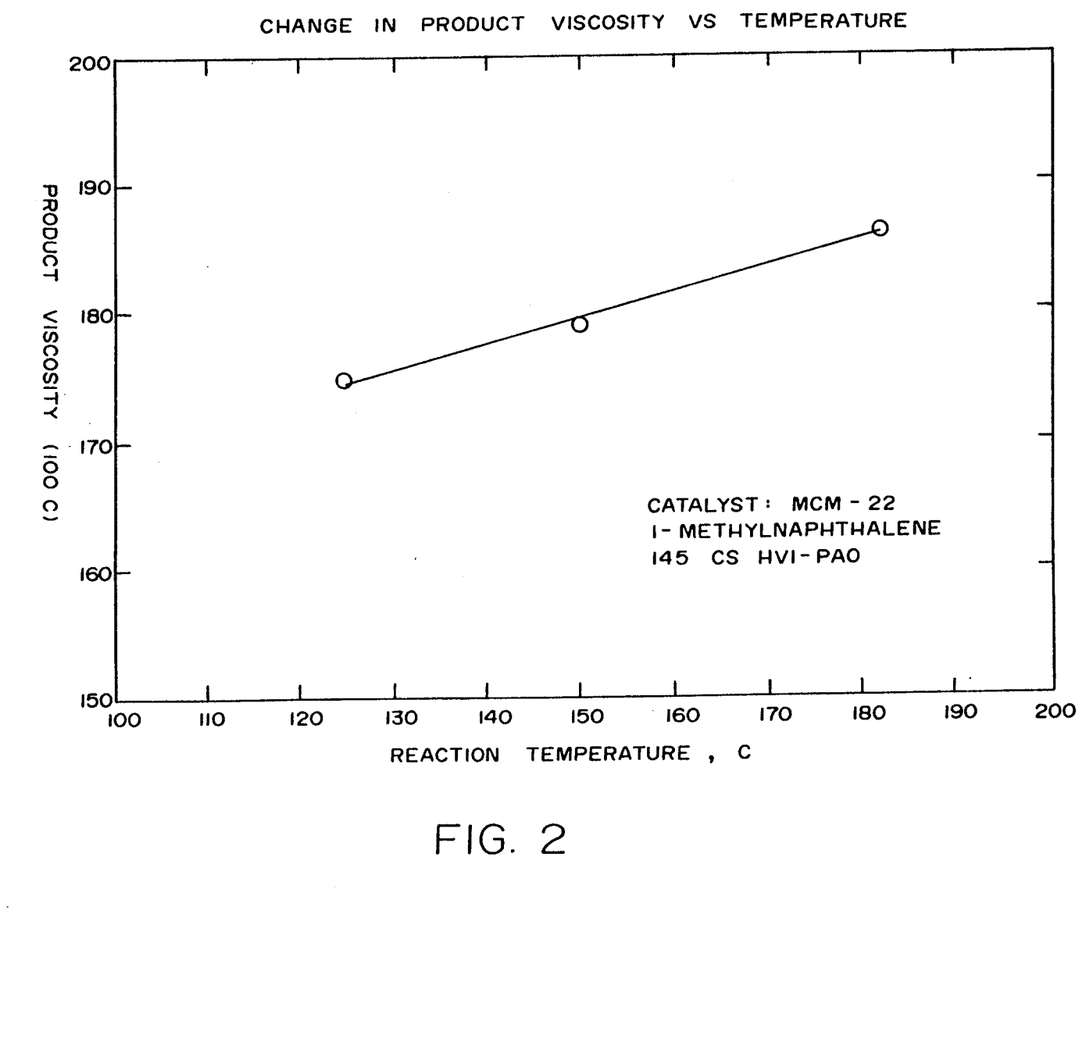
FIG. 2 shows the relationship between reaction temperature and the increase in product viscosity after reaction.

FIG. 1 shows the relationship between the reaction temperature and the corresponding influence on reducing the viscosity loss during the termal stability test. FIG. 2 shows the relationship between reaction temperature and the increase in product viscosity after reaction.

TABLE 8

Reaction Conditions and Product Properties
1-Methylnaphthalene and 145 CS HVI-PAO With MCM-22

| Example | Feed | 18 | 19 | 20 |
|---|---|---|---|---|
| Reaction Temperature, °C. | | 125 | 150 | 182 |
| Reaction Time, Days | | 3 | 1 | 2 |
| MCM-22, g. | | 2 | 2 | 2 |
| 145 CS HVI-PAO, g. | | 25 | 25 | 25 |
| 1-MeNaphthalene, g. | | 10 | 10 | 10 |
| Viscosity 40° C., cS | 1412 | 1883 | 1987 | 2149 |
| Viscosity 100° C., cS | 145 | 174 | 179 | 186 |
| Viscosity Index | 215 | 213 | 211 | 209 |
| Bromine Number | 4.8 | 2.1 | 2.2 | 3.1 |
| Viscosity Loss, %, 300° C.-24 hrs | 76 | 48 | 46 | 31 |

EXAMPLES 21-23

Similar alkylation reaction: were also conducted with a 9.3 cS HVI-PAO again using 1-methylnaphthalene as the aromatic compound. These results are shown in Table 9 below. Since the average molecular weight of the 9.3 cS HVI-PAO is much lower than the 145 cS HVI-PAO, the contribution of the unhydrogenated double bond is much larger. Therefore there is a greater percentage reduction in the bromine number and a measurable increase in the yield of the alkylated product. Typical increases in weight, due to the addition of the aromatic, are about 10%. The largest extent of reaction is noted in Examples 23 and 24 where about 80% of the reaction was completed.

Carbon 13 NMR was used to confirm the presence of an aromatic function in the HVI-PAO molecule. In addition to this reaction, some structural isomerization of the HVI-PAO molecules was noted.

TABLE 9

Reaction Conditions and Product Properties
1-Methylnaphthalene and 9 CS HVI-PAO With MCM-22

| Example | Feed | 21 | 22 | 23 |
|---|---|---|---|---|
| Reaction Temperature, °C. | | 150 | 180 | 193 |
| Reaction Time, Days | | 1 | 1 | 2 |
| MCM-22, g. | | 2 | 2 | 2 |
| 9 CS HVI-PAO, g. | | 25 | 20 | 20 |
| 1-MeNaphthalene, g. | | 10 | 10 | 10 |
| Alkylated Product, g. | | 27.3 | 21.8 | 22.5 |
| Weight Increase, % | | 10.1 | 9.0 | 12.5 |
| Extent of Reaction, by redtn. of Bromine No. | | 60 | 81 | 80 |
| Viscosity 40° C., cS | 50.6 | 128.9 | 207.7 | 243.3 |
| Viscosity 100° C., CS | 9.3 | 16.5 | 22.4 | 23.6 |
| Viscosity Index | 170 | 138 | 131 | 121 |
| Bromine Number | 18.8 | 7.6 | 3.6 | 3.8 |

We claim:

1. A process for the preparation of alkylaromatic compounds, comprising: alkylating at least one alkylatable aromatic compound and with an alkylating agent comprising an olefinic hydrocarbon oligomer having a branch ratio less than 0.19 in the presence of a solid, porous acidic alkylation catalyst comprising a crystalline mater al characterized by an X-ray diffraction pattern including values substantially as set out in Table 1 of the specification to produce an alkylated aromatic hydrocarbon product.

2. A process according to 1 in which the synthetic porous crystalline material is characterized by an X-ray diffraction pattern including values substantially as set forth in Table 2 of the specification.

3. A process according to 1 in which the synthetic porous crystalline material is characterized by an X-ray diffraction pattern including values substantially as set forth in Table 3 of the specification.

4. A process according to 1 in which the synthetic porous crystalline material is characterized by an X-ray diffraction pattern including values substantially as set forth in Table 4 of the specification.

5. A process according to 1 in which the synthetic porous crystalline material has a composition comprising the molar relationship $$X_2O_3:(n)YO_2,$$

wherein n is at least about X is a trivalent element and Y is a tetravalent element.

6. A process according to 1 in which the synthetic porous crystalline material has the structure of MCM 22.

7. A process according to claim 1 in which the alkylation is carried out under alkylation conditions comprising a temperature between −30° and 350° C., and a pressure between 700 and 7000 kPa.

8. A process according to claim 1 in which the olefin oligomer comprises the reaction product of the oligomerization under oligomerization conditions of a $C_2$–$C20$ 1-alkene in contact with supported reduced metal oxide oligomerization catalyst comprising a lower valence state form of at least Group VIB metal.

9. A process according to claim 8 in which the supported reduced metal oxide catalyst comprises reduced chromium oxide on silica support.

10. A process according to claim 1 in which the oligomerization conditions comprise a temperature between 90° and 250° C.

11. A process according to claim 1 in which the olefin oligomer comprises a $C_{30}$ to $C_{13000}$ liquid lubricant oligomer having a weight average molecular weight between 280 and 450,000 and number average molecular weight between 280 and 180,000.

12. A process according to claim 11 in which the molecular weight distribution of the olefin oligomer is rom 1.00 to 5.

13. A process according to claim 12 in which the molecular weight distribution of the olefin oligomer is from 1.01 to 3.

14. A process according to claim 9 in which the viscosity of the olefin oligomer from 1.5 to 7500 cs at 100° C.

15. A process according to claim 9 in which the olefin oligomer comprises a $C_{30}$ to $C_{1000}$ oligomer having a viscosity of up to 1000 cs at 100° C.

16. A process according to claim 9 in which the oligomerization conditions comprise a temperature below about 90° C. and the olefin oligomer comprises hydrocarbons which have a branch ratio below 0.19 and a viscosity at 100° C. which is from 100 to 20,000 cS.

17. A process according to claim 16 in which the olefin oligomer has a weight average molecular weight from 15 000 to 200,000 and number average molecular weights from 5,000 to 50,000 with a molecular weight distribution from about 1 to about 5.

18. A process according to claim 17 in which the olefin oligomer is stable under high temperature, high shear rate conditions of 150° C. and a shear rate of one million ($10^6$) reciprocal seconds.

19. A process according to claim 1 in which the aromatic compound comprises a monocyclic aromatic hydrocarbon.

20. A process according to claim 19 in which the aromatic hydrocarbon is benzene or an alkylbenzene.

21. A process according to claim 1 in which the aromatic compound comprises a bicyclic aromatic hydrocarbon.

22. A process according to claim 21 in which the aromatic hydrocarbon is naphthalene or a substituted napthalene.

23. A process according to claim 1 in which the aromatic hydrocarbon comprises anthracene.

24. A process according to claim 1 in which the aromatic compound is phenol, anisol or naphthol.

* * * * *